US012379126B2

(12) United States Patent
Li et al.

(10) Patent No.: US 12,379,126 B2
(45) Date of Patent: Aug. 5, 2025

(54) Q-LEARNING BASED MODEL-FREE CONTROL METHOD FOR INDOOR THERMAL ENVIRONMENT OF AGED CARE BUILDING

(71) Applicants: Qingdao University of Technology, Qingdao (CN); Zhejiang University, Hangzhou (CN)

(72) Inventors: Yanxue Li, Qingdao (CN); Wenya Xu, Qingdao (CN); Yue Gu, Qingdao (CN); Yang Xu, Qingdao (CN); Weijun Gao, Qingdao (CN)

(73) Assignees: Qingdao University of Technology, Qingdao (CN); Zhejiang University, Hangzhou (CN)

( * ) Notice: Subject to any disclaimer, the term of this patent is extended or adjusted under 35 U.S.C. 154(b) by 474 days.

(21) Appl. No.: 17/876,165

(22) Filed: Jul. 28, 2022

(65) Prior Publication Data

US 2023/0304689 A1    Sep. 28, 2023

(30) Foreign Application Priority Data

Mar. 21, 2022   (CN) .......................... 202210274212.3

(51) Int. Cl.
*F24F 11/63*   (2018.01)
*F24F 11/49*   (2018.01)
*G16H 40/20*   (2018.01)

(52) U.S. Cl.
CPC .............. *F24F 11/63* (2018.01); *F24F 11/49* (2018.01); *G16H 40/20* (2018.01)

(58) Field of Classification Search
CPC .................................. F24F 11/49; F42F 11/63
See application file for complete search history.

(56) References Cited

U.S. PATENT DOCUMENTS

| 11,783,203 | B2* | 10/2023 | Camilus ................. G06F 30/13 |
| | | | 700/291 |
| 11,804,301 | B2* | 10/2023 | de Zambotti .......... G16H 20/30 |
| 2015/0268641 | A1* | 9/2015 | Balakrishnan ..... G05D 23/1931 |
| | | | 700/90 |
| 2018/0073760 | A1* | 3/2018 | Smith ...................... F24F 11/30 |
| 2020/0200416 | A1* | 6/2020 | Granger ................. G16H 40/67 |

(Continued)

*Primary Examiner* — Mohammad Ali
*Assistant Examiner* — Vincent W Chang
(74) *Attorney, Agent, or Firm* — Porus IP LLC

(57) ABSTRACT

The present disclosure provides a Q-learning based model-free control method for an indoor thermal environment of an aged care building and belongs to the technical field of building environment control. According to the present disclosure, the monitored indoor temperatures of individual users and the heart rate and systolic pressure data of the aged are used as input data to a constructed Q-learning model, thus outputting a running control policy for a heating, ventilation and air conditioning system in the corresponding building. As a result, the control efficiency of the indoor temperature and the energy efficiency of the heating, ventilation and air conditioning system are improved. Compared with a traditional control model, the reinforced learning method based on the Q-learning theory can realize more accurate prediction on the cardiovascular health risk of the aged and can create a dynamic indoor thermal environment more suitable for the physical health of the aged.

6 Claims, 5 Drawing Sheets

(56) References Cited

U.S. PATENT DOCUMENTS

| | | | |
|---|---|---|---|
| 2020/0211062 A1* | 7/2020 | Kossakovski | G06Q 30/0271 |
| 2020/0258618 A1* | 8/2020 | Zhou | G16H 10/60 |
| 2020/0342968 A1* | 10/2020 | Avinash | G16H 50/30 |
| 2021/0391079 A1* | 12/2021 | Clifton | A61B 5/7275 |

* cited by examiner

Q-LEARNING BASED MODEL-FREE CONTROL METHOD FOR INDOOR THERMAL ENVIRONMENT OF AGED CARE BUILDING

CROSS REFERENCE TO RELATED APPLICATION

This patent application claims the benefit and priority of Chinese Patent Application No. 202210274212.3, filed on Mar. 21, 2022, the disclosure of which is incorporated by reference herein in its entirety as part of the present application.

BACKGROUND

Related Field

The present disclosure relates to the technical field of building environment control, and more particularly, to a Q-learning based model-free control method for an indoor thermal environment of an aged care building oriented to the improvement of the cardiovascular health of the aged based on the reinforced learning theory.

Related Art

With the improvements in the living quality and the medical level, people are getting older and the population aging problem has become the focus of increasing concern by people. Research has shown that cardiovascular diseases have taken first place among total causes of death of Chinese urban and rural residents and high blood pressure has been a leading cause of the cardiovascular diseases. Exposure to the environmental temperature will directly affect the thermal equilibrium process of the blood circulation system of the human body. The aged may have reduced skills in of managing the thermal equilibrium process of the body and may suffer from cardiovascular diseases at a high rate. The statistics have indicated that people, especially the aged, may spend about 90% of their time indoors. An indoor thermal environment has an important impact on people's health. With the proposed plan for a Healthy China 2030 and Assessment Standard for Green Building GB/T50378-2019, it is of great significance to provide a healthy and comfortable indoor thermal environment of an aged care building to the aged.

Compared with an ordinary building, the users of the aged care building have special physical and psychological needs, and the comfort of the dwelling environment and the health of the living space are extremely important goals. At present, Chinese aged care building design is in its infancy. Nevertheless, increasingly serious aging poses higher requirements on the comfort of the indoor thermal environment of the aged care building. Meanwhile, the development of technologies such as the Internet and artificial intelligence provides reliable support for smart operation of the aged care building.

The aged is a special group in comparison to the young. With increasing age, the changes in various functions of the body may affect the regulation of the whole body. Physical health will be affected in different indoor environments. In view of the physiological needs of the aged, it is of great significance to improve the living environment of the aged and improve the comfort of the indoor thermal environment of the aged care building. The human body is homothermal and can exchange and transfer energy with the surroundings in such forms of heat conduction, heat radiation and convective heat exchange. When the surroundings are extremely cold or hot, the thermoregulatory system of the human body can maintain the thermal balance of the human body by way of blood flow, perspiration and heat production on the skin surface.

Blood pressure is the pressure of flowing blood against the sidewall of the blood vessel. Heart rate is the rate at which the heart outputs blood. The change in body temperature may affect the vasomotion and blood flow and thus affect changes in blood pressure and heart rate. Research has showed that when the blood pressure rises, the blood vessel of the human body may thicken to increase the contact area with the blood and reduce the pressure. However, when the blood pressure changes like this for a long time, continuous thickening of the blood vessel may cause the wall of the blood vessel to thicken, resulting in narrowing of the blood vessel, which in turn promotes the blood pressure to rise. Repeated interactions make the blood vessel reshape. It needs to be noted that the rising of the central blood pressure not only leads to changes in the blood pressure and the vascular structure of great vessels but also affects the blood pressure and the vascular structure of small arteries and arterioles. Blood perfusion induced by an extremely high blood pressure may cause damage to such target organs as the heart, brain and kidney.

As the aged gets older, various body functions gradually degrade and the ability for activities is damaged. Thus, the indoor space becomes the major activity space for the aged. Real-time monitoring data of the blood pressure and the heart rate can well reflect the physiological response of the aged in different indoor thermal environments and monitor the change in the cardiovascular health of the aged. The research found that the blood pressure is in significantly negative correlation to the indoor temperature. The blood pressure may be large when the temperature is low in the morning and evening. Especially, the systolic pressure may be greatly affected by the indoor temperature, and more obvious changes may be found in the aged than in the young. The heart rate is positively related to the indoor temperature. When the temperature is low, the heart rate is low. When the temperature is high, the heart rate is high. When the heart rate is low, the heart has less blood pressure output. If it continues for a long time, insufficient blood supply may occur easily, and various parts of the body may be affected. For the aged, the systolic pressure normally ranges from 90 to 140 mmHg; the heart rate normally ranges from 60 to 100 beats per minute. The ideal heart rate ranges from 55 to 70 beats per minutes. When the heart rate of a hypertension patient exceeds 80 beats per minute, the heart rate needs to be reduced.

To sum up, the aged is more prone to the stimulus of change in the thermal environment than the young. Under a cold stimulus, the peripheral blood vessels of the aged are constricted and the skin blood flow is reduced. Moreover, less metabolism occurs when the blood vessels are constricted less. To meet the demand on the blood volume by the body, the heart of the aged may provide a great blood output, causing a large burden to the heart. Under a thermal stimulus, the peripheral blood vessels of the aged are dilated and the skin blood flow increases. Compared with the young, the aged has less overall blood flow distribution, less blood output of the heart, and less blood distribution in organs such as the kidney.

Existing aged care buildings neglect the influence of the indoor temperature on the cardiovascular health of the aged and lack more flexible indoor temperature control means.

Therefore, to improve the cardiovascular health level of the aged, one of the keys to the defects and problems in the prior art is to improve the comfort of the indoor thermal environment of the aged care building according to the physiological parameter characteristics of the cardiovascular health of the aged.

BRIEF SUMMARY

An objective of the present disclosure is to provide a Q-learning based model-free control method for an indoor thermal environment of an aged care building to make up for the deficiencies of the prior art.

Human learns by interacting with the environment. Likewise, Q-learning, namely a temporal-difference algorithm under an off-track policy, is proposed as one of reinforced learning methods. This method is the reinforced learning algorithm based on values rather than an environmental model. Thus, a user does not need to model the external environment in detail and only needs to provide enough satisfactory training samples. An optimal policy set can be obtained through the interaction between an agent and the environment, and the convergence characteristics thereof have been verified. Therefore, the present disclosure proposes optimized control of a heating, ventilation and air conditioning system based on indoor monitored temperatures and the normal ranges of monitored physiological parameters using the Q-learning algorithm of reinforced learning.

To achieve the above objective, the present disclosure is implemented by using the following technical solutions.

A Q-learning based model-free control method for an indoor thermal environment of an aged care building includes the following steps:

S1: determining related influencing factors for the indoor thermal environment and influencing factors for the cardiovascular health of the aged, the related influencing factors for the indoor thermal environment including a controlling variable and a controlled variable for the thermal environment in a room and the influencing factors for the cardiovascular health of the aged including a systolic pressure and a heart rate; and preprocessing collected data as training sample data;

S2: constructing a building indoor thermal environment control model and setting an indoor temperature between 18° C. and 24° C.;

S3: constructing a Q-learning model, specifying a state variable and an action variable of control and a constraint and a reward and punishment mechanism of a state and action value function, and training the Q-learning model with the training sample data to obtain a trained Q-learning model; and S4: importing data to be processed to the trained Q-learning model as learning samples and obtaining an optimal control running policy by iterative updating and repeated training.

Further, S1 may include:

S1-1: determining cardiovascular health parameters associated with the indoor thermal environment and selecting the systolic pressure and the heart rate as real-time monitoring data; and S1-2: analyzing the influencing factors for the indoor thermal environment, determining the controlling variable and the controlled variable of the thermal environment in the room, and collecting indoor temperatures corresponding to time information in the building.

More specifically:

(1) The data of cardiovascular physiological parameters (including heart rate RH(t) and systolic pressure SBP(t)) of the aged in the indoor environment are collected, thereby realizing dynamic monitoring of the cardiovascular health condition of the aged. During the collection of sample data, it is required that the individual characteristics such as body weight and age of the aged are recorded in detail. Real-time data of the heart rate, the blood pressure and the like of the subject are acquired accurately, and a corresponding indoor temperature is recorded by a temperature and humidity recorder. An indoor temperature suitable for the living of the aged is determined based on the normal ranges of the heart rate and the blood pressure.

(2) The indoor temperature $T_{in}(t)$ of the aged care building is monitored and acquired in real time, which corresponds to the heart rate and systolic pressure data at each time.

(3) The indoor temperature $T_{in}(t)$, the heart rate RH(t) and the systolic pressure SBP(t) are used as state variables of a Q model.

A preprocessing method for the collected data may be as follows:

(1) Missing values of the data are supplemented. Some information such as temperatures and heart rates at a few times may be lost or missing for several reasons such as equipment faults during data collection. This part of data may be filled by cubic spline interpolation. This method involves a small amount of calculation and has high calculation accuracy. For example, in the matlab software environment, the corresponding interp1 function and spline function may be employed for filling.

(2) Outliers are processed. Outliers are data departing from most of the data in a data set. The processing of the outliers mainly includes direct deletion, replacement with a mean value or other statistics, and the like. The outliers are supplemented as missing values here. To confirm the outliers, a reasonable range $[\mu-3\sigma, \mu+3\sigma]$ of the collected data is confirmed by using $3\sigma$, namely the standard deviation method, where $\mu$ represents the mean value of the data set, and $\sigma$ represents the standard deviation. The data exceeding the range are picked out for replacement and filling.

Further, S2 may include:

S2-1: considering the physiological needs and the health characteristics of the aged, comprehensively assessing the influences of heart rate RH(t) and systolic pressure SBP(t) monitored in real time on the cardiovascular health based on an ideal heart rate range of 55-80 beats per minute and a normal systolic pressure range of 90-140 mmHg, and deriving a health risk function: Unhealthy=aSBP(t)+bRH(t), where a and b are influence coefficients, and a>b;

calculating a user reward function R by Equation (1):

$$R(t)=\lambda R_{Tin}(t)+\theta R_{Unhealthy}(t) \quad (1)$$

where $\lambda$ and $\theta$ are reward factors, $0<\theta<\lambda<1$, representing proportions of the influences of an indoor temperature and the cardiovascular health parameters of the aged in optimized control; $\lambda+\theta=1$, ($\lambda>\theta$); $R_{Tin}(t)$ represents considering a reward value resulting from a change in indoor temperature, and $R_{Unhealthy}(t)$ represents comprehensively considering the influences of the cardiovascular health parameters of the aged on the state determination of an agent; and S2-2: in consideration of the changing character of the heart rate and the systolic pressure, selecting a mean value to calculate the values of the heart rate and the systolic pressure within a certain time period and calculating the mean value of the heart rate by Equation (2):

$$\overline{RH}_{(t)} = \frac{1}{N}\sum_{i=1}^{N}RH_{(i)} \quad (2)$$

where N represents the number of heart rate data collected in the time period; i=1, 2, 3, . . . , N. $RH_{(i)}$ represents specific heart rate sample data; $\overline{RH}$ represents a mean value of the heart rate sample data. The systolic pressure SBP(t) is calculated by an equation similar to Equation (2).

Further, in S3:

The indoor thermal environment is associated with the data of the cardiovascular physiological parameters of the aged so that the Q-learning model can calculate the reward function R based on the monitored indoor temperature and the health risk function Unhealthy of the aged, thus realizing effective control on an air conditioning system. The heating power of a heating, ventilation and air conditioning system is taken as action control, where a maximum indicates the maximum heating power q of the heating, ventilation and air conditioning system, and a minimum, which is 0, indicates that the heating, ventilation and air conditioning system is in dormant state. That is, the power consumption of the heating, ventilation and air conditioning system is taken as the output of the Q-learning model. This step may specifically include:

S3-1: importing a collected data set of the cardiovascular health parameters of the aged to the Q-learning model for running;

S3-2: selecting, by the agent, greedy policy for making a decision;

S3-3, updating, by the agent, the value of Q by Equation (3):

$$Q(S_t, A_t) \leftarrow Q(S_t, A_t) + \alpha\left[R_{t+1} + \gamma \max_a Q(S_{t+1}, a) - Q(S_t, A_t)\right] \quad (3)$$

where t is a current time; α is a learning rate a trustworthiness degree of an upgraded portion; γ represents a current attenuation rate of a future value of Q; S represents an environmental state; A represents an action executable by the agent; R represents the reward function defined as needed; π represents a policy set of the agent;

$S_{t+1}$ represents next state observed after an action policy is performed in the current state; $R_{t+1}$ represents a reward obtained; and s and Q (s, a) are updated;

S3-4: in case of bad convergence effect of a learning process determined by a Q table and a learning number threshold, continuously adjusting parameters α and γ continuously in combination with running of the model, which allows the whole learning process to realize better convergence effect; and S3-5: repeating the above steps for n times until an optimal policy set π having a maximum cumulative reward value R, namely a control running policy, is obtained by learning.

Further, in S3, the Q-learning model is built by discretizing the continuous state variable and action variable according to a target problem, allowing the agent to continuously interact with the environment to update the Q table using reward values obtained by taking corresponding actions in different states, and mastering a solution of how to get the highest reward by multiple iterations, namely, obtaining the optimal policy set of accomplishing the target problem.

Further, in S3, the state and action value function of Q-learning is expressed as:

$$Q(S_t, A_t) \leftarrow Q(S_t, A_t) + \alpha\left[R_{t+1} + \gamma \max_a Q(S_{t+1}, a) - Q(S_t, A_t)\right] \quad (3)$$

where t is a current time; α is a learning rate, representing a trustworthiness degree of an upgraded portion; γ represents a current attenuation rate of a future value of Q; S represents an environmental state; A represents an action executable by the agent; R represents the reward function defined as needed; π represents a policy set of the agent.

The parameters α and γ are adjusted, where α∈ (0, 1], and γ∈ (0, 1] and therefore, the whole learning process is caused to converge correctly.

The training sample data are input to the Q-learning model for training; the reward values of different actions in different states are updated by iterations until the optimal state and action value function is obtained; and the trained Q-learning model is saved.

Compared with the prior art, the present disclosure has the following advantages and beneficial effects.

The present disclosure is oriented to the improvement of the cardiovascular health of the aged based on the reinforced learning theory. According to the present disclosure, the monitored indoor temperatures of individual users and the heart rate and systolic pressure data of the aged are used as input data to the constructed Q-learning model, thus outputting a running control policy for the heating, ventilation and air conditioning system in the corresponding building. As a result, the control efficiency of the indoor temperature and the energy efficiency of the heating, ventilation and air conditioning system is improved. Compared with a traditional control model, the reinforced learning method based on the Q-learning theory can realize a more accurate prediction of the cardiovascular health risk of the aged and can create a dynamic indoor thermal environment more suitable for the physical health of the aged.

The present disclosure allows for effective improvement of the thermal comfort of the living environment of the aged and prevention of the cardiovascular diseases of the aged.

DETAILED DESCRIPTION OF VARIOUS EMBODIMENTS

The technical solutions of the present disclosure will be further described below by way of examples with reference to the accompanying drawings.

Example 1

Figure 2:
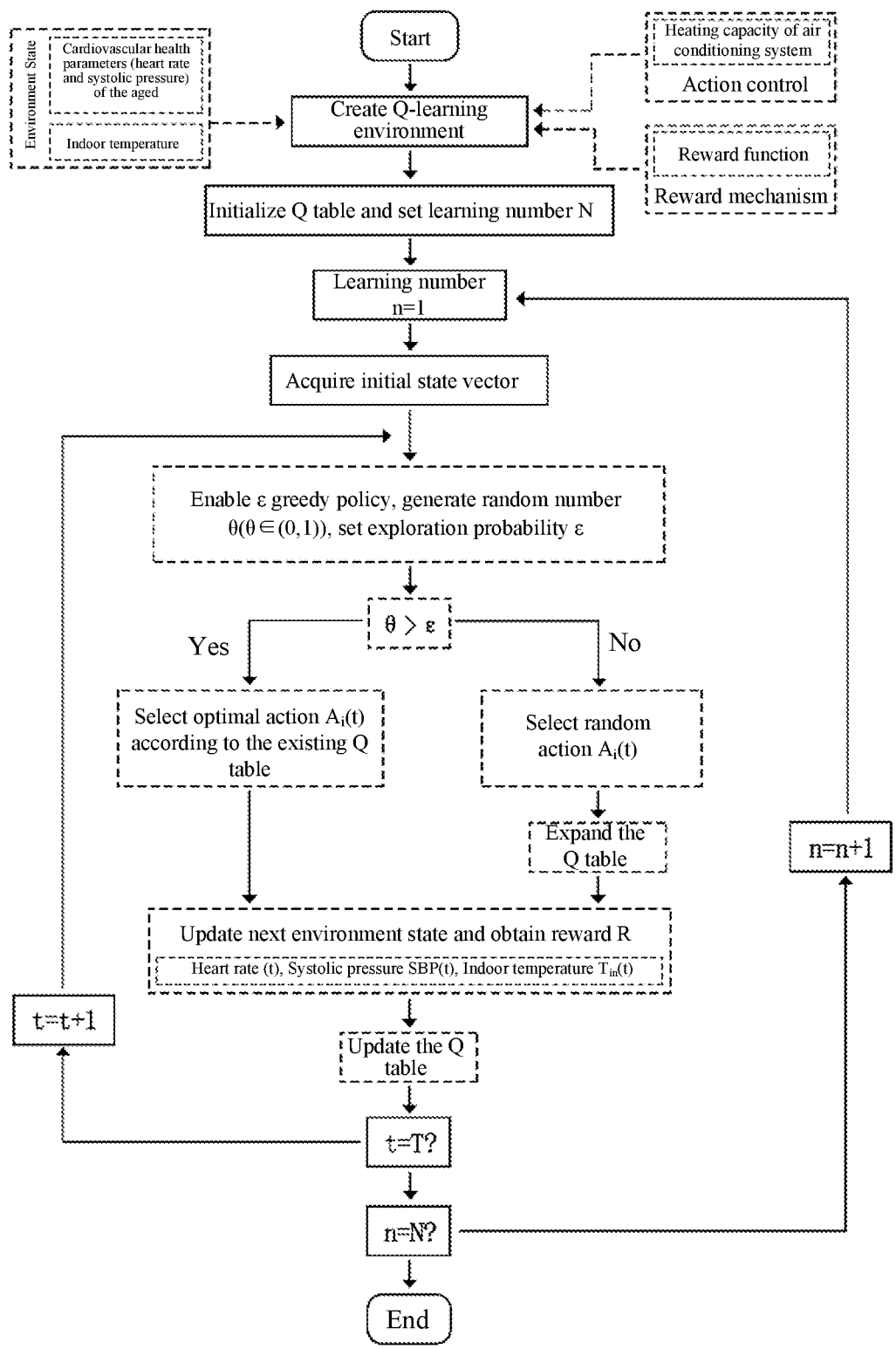
FIG. 2 is a basic flowchart of the present disclosure.
Figure 3:
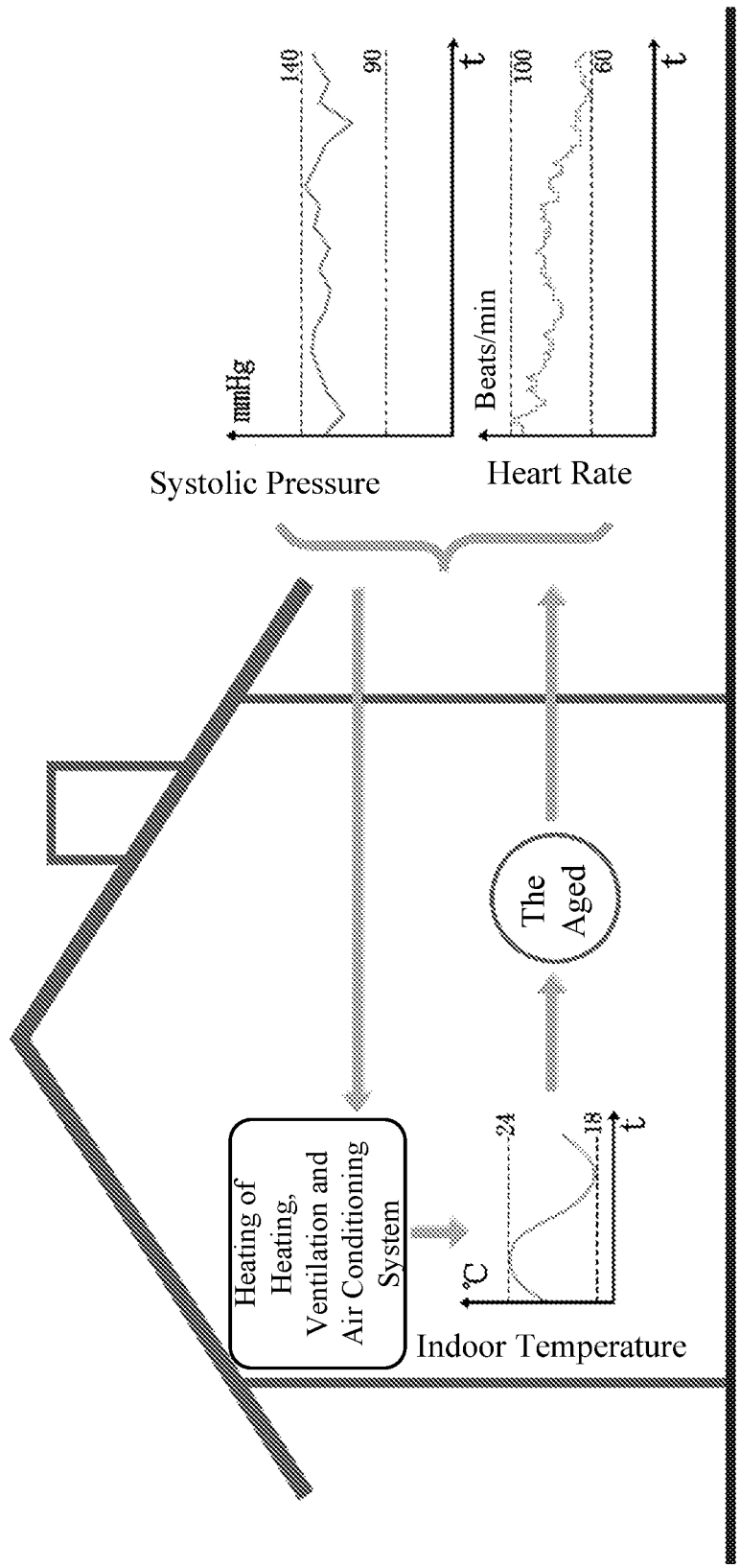
FIG. 3 is a schematic diagram of the influence of an indoor thermal environment on the cardiovascular health of the aged.

A Q-learning based model-free control method for an indoor thermal environment of an aged care building (the specific flow is as shown in FIG. 2) includes the following steps:

(1) Influencing factors for the cardiovascular health of the aged are analyzed, from which the influencing factors associated with the indoor thermal temperature are determined (the influence of the indoor thermal environment on the cardiovascular health of the aged is as shown in FIG. 3).

A controlling variable and a controlled variable convenient to realize among influencing factors for the indoor thermal environment are analyzed. That is, a comfortable indoor temperature has a significance influence on the cardiovascular health of the aged.

The building indoor thermal environment data (namely, indoor temperature $T_{in}(t)$) changing with time t in a certain time period and the data of the physiological parameters (including heart rate RH(t) and systolic pressure SBP(t)) of the aged are collected.

The specific collection process of the cardiovascular physiological health parameters of the aged is as follows:

Before the collection starts, the age, gender, height and weight of the aged are recorded in detail. The subject is required not to drink alcohol during measurement.

During collection, the subject is required to wear Polar H10 heart rate chest belt. The heart rate can be monitored in real time on a mobile phone platform. The chest belt is taken down at night and the heart rate data monitored are exported from a computer terminal. The blood pressure is measured using H7-CMS06C dynamic blood pressure monitor. It starts from getting up in the morning, once every 2 hours. The last measurement is performed before sleeping at night. In the whole collection process, the indoor temperature is recorded in real time using TANDD temperature and humidity recorder.

After the data collection is finished, the heart rate and the blood pressure need to correspond to the indoor temperature at the same time. It can be used to study the changes in the heart rate and the blood pressure at different indoor temperatures. The indoor temperature suitable for living of the aged is determined according to the normal heart rate range and the normal blood pressure range.

The monitored and collected data are preprocessed.

Figure 4:
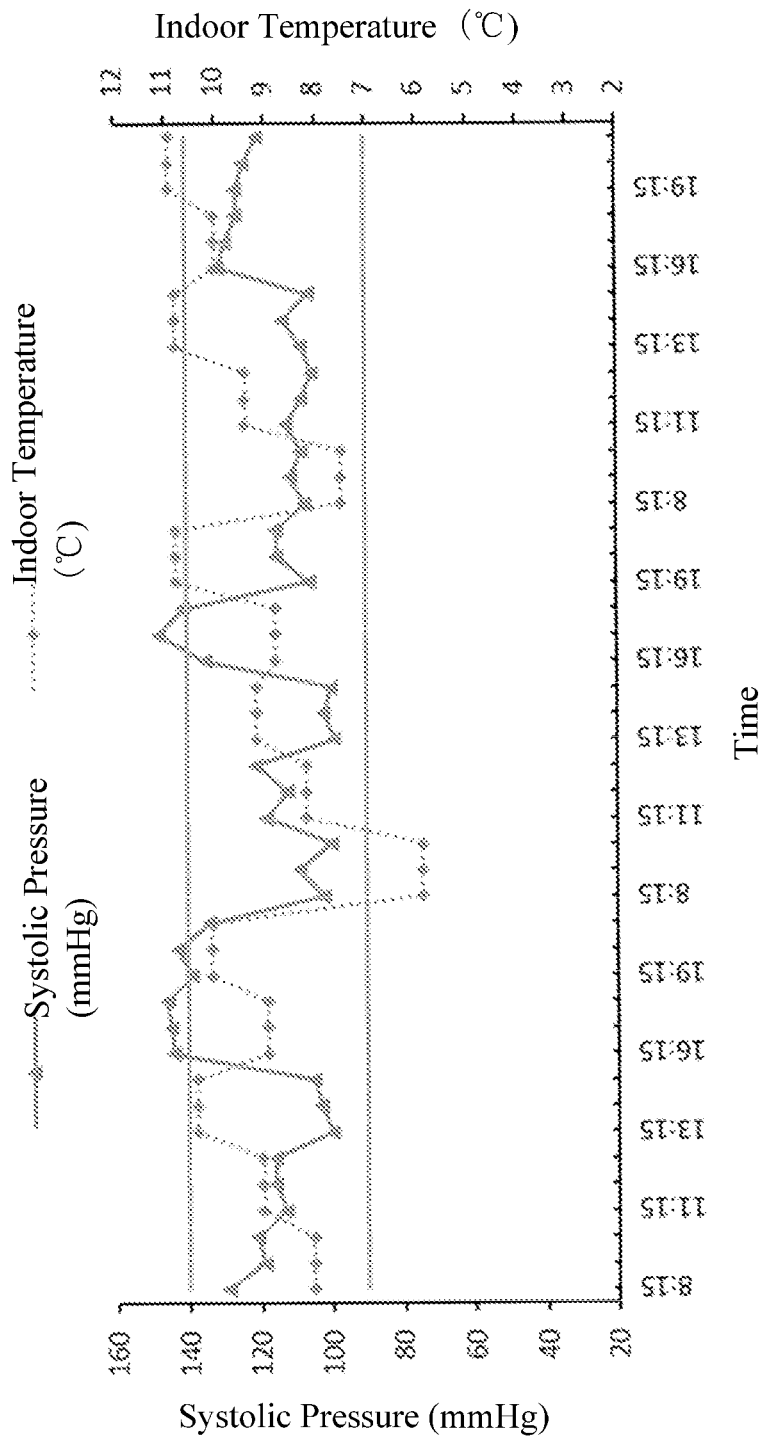
FIG. 4 shows a changing relationship between the blood pressure of an old person and the temperature by daylight in winter.
Figure 5:
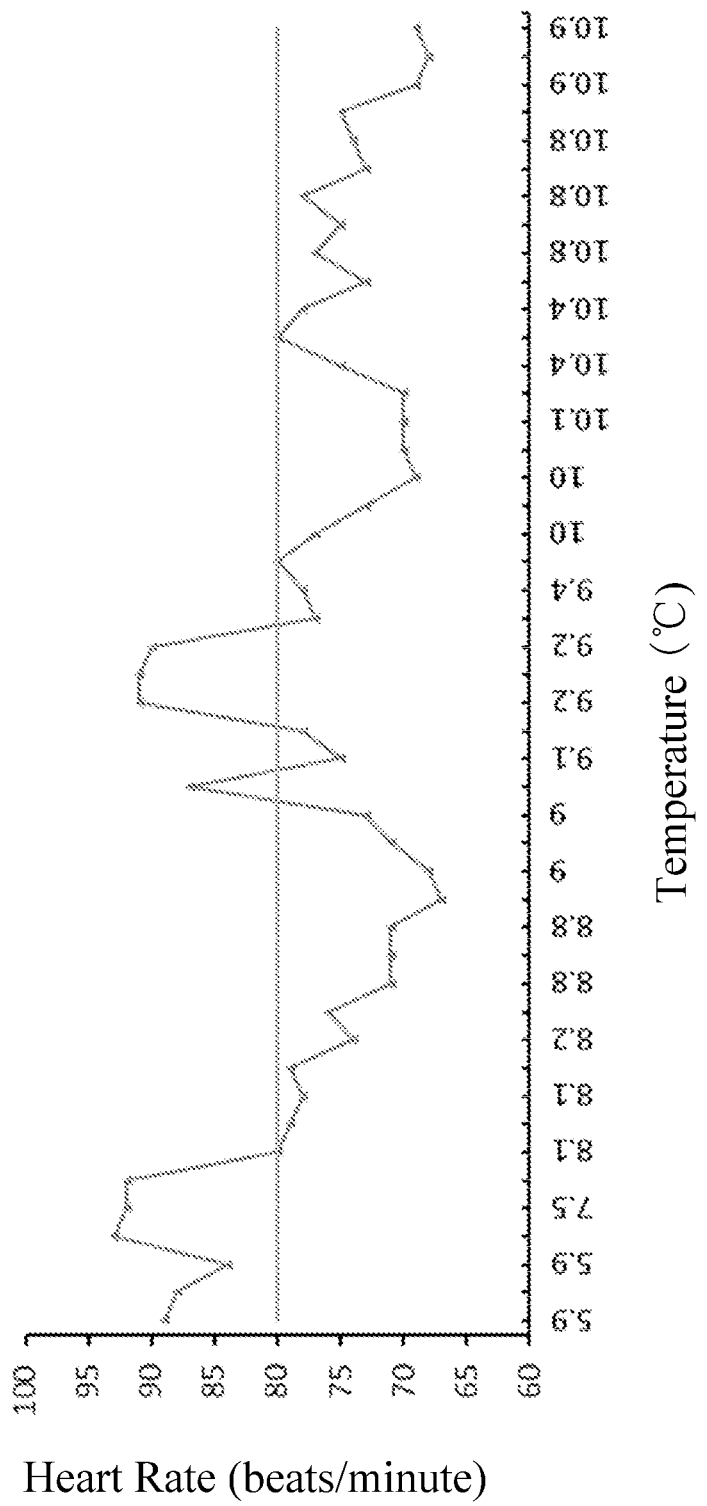
FIG. 5 shows changes in the heart rate of an old person at different temperatures in winter.

FIG. 4 shows a changing relation between the blood pressure of an old person and the temperature by daylight in winter in the process of experiment. Data analysis indicates that when the indoor temperature is below the comfortable temperature range, the old person has a high blood pressure which even exceeds the normal blood pressure range. FIG. 5 shows changes in the heart rate of the aged at different temperatures in winter. When the temperature is low, the heart rate fluctuates significantly. When the temperature gradually rises, the heart rate tends to be stable.

Figure 1:
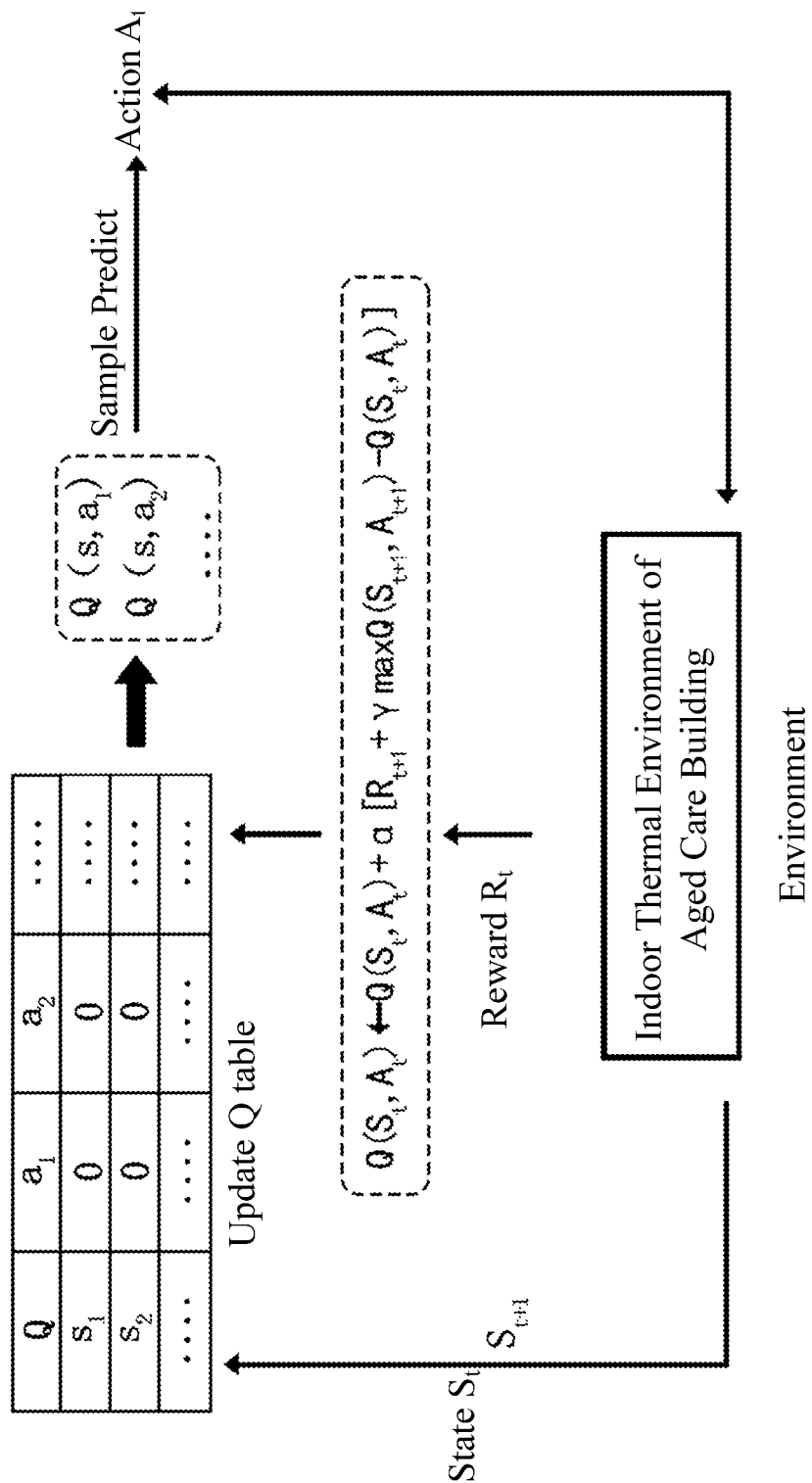
FIG. 1 is a structural diagram of a Q-learning model.

(2) A optimized control model based Q-learning (the basic flowchart of the model is as shown in FIG. 1) is constructed. The optimized problem of a control system is modeled as a Markov decision-making process.

Firstly, an optimization objective is specified. It should be guaranteed that the monitored physiological parameters are kept in normal ranges. Considering that the ideal heart rate is 55-70 beats per minute and the heart rate of a hypertension patient shall not exceed 80 beats per minute, a standard heart rate range is set to 55-80 beats per minute. The standard systolic pressure range is set to 90-140 mmHg and the comfortable indoor temperature is set to 18° C.-24° C.

Secondly, the physiological parameters heart rate RH(t), systolic pressure SBP(t) and indoor temperature $T_{in}(t)$ related to the cardiovascular health of the aged are determined as a state observation space, namely S=[RH(t), SBP(t), $T_{in}(t)$].

Thirdly, the indoor temperature is convenient to control and thus used as a controllable variable. The heating power (q) of a heating, ventilation and air conditioning system is a controllable variable (a controlled variable), namely action space A (action variable).

Adapting to the characteristics of the Q-learning model, the action and state spaces are discretized, where A=[0, 0.25q, 0.5q, 0.75q, q]. For ease of calculation, the observation factors of the state space are similarly divided into 5 segments at equal intervals according to a variation range of the monitored data. These forms a state space matrix.

A system state and a Q table are initialized.

In range (0,1], α and γ are set, for example, α=0.5 and γ=1.

The number of cyclical iterations of model exploration is set as episode=n, n∈N⁺.

A reward function corresponds to a control objective to determine a reward value that can be obtained by an action taken under the current state variable. The reward function R is set to be composed of two parts. The reward coefficients of the two parts meets the relationship λ+θ=1, (λ>θ), specifically expressed as Equations (1) and (4):

$$R(t)\lambda R_{Tin}(t)+\theta R_{Unhealthy}(t) \quad (1)$$

$$R_{Unhealthy}(t)=ar_{SBP(t)}+br_{RH(t)} \quad (4)$$

One part is the influence Rd of temperature. It ensures that the indoor temperature in a comfortable range is created at the sacrifice of low energy consumption. A lower limit temperature is set as $T_{lower\ bound}$=18° C. and an upper limit temperature is set as $T_{upper\ bound}$=24° C. A corresponding penalty coefficient ω represents the influence on the optimization objective caused by the room temperature falling outside the comfortable range, as shown by Equation (5):

$$R_{Tin}(t) = \begin{cases} -\omega[T_{in}(t) - T_{lower\ bound}]^2, & \text{if } T_{in}(T) < 18° C. \\ -\omega[T_{in}(t) - T_{upper\ bound}]^2, & \text{if } T_{in}(T) < 24° C. \\ 0, & \text{if } 18° C. \leq T_{in}(T) \leq 24° C. \end{cases} \quad (5)$$

The other part is the influence $R_{Unhealthy}$ of changes in the cardiovascular health parameters of the aged. A health reward function is derived based on the ideal range of heart rate RH(t) of 55-80 beats per minutes and the normal range of systolic pressure SBP(t) of 90-140 mmHg. Since the selected cardiovascular health parameters change greatly within sampling time Δt, a mean value is selected for calculation. For example, the mean value of the heart rate is calculated by Equation (2):

$$\overline{RH}_{(t)} = \frac{1}{N}\sum_{i=1}^{N}RH_{(i)} \quad (2)$$

where N represents the number of heart rate data collected in the time period; i=1, 2, 3, . . . , N; $RH_{(i)}$ represents specific heart rate sample data; $\overline{RH}$ represents a mean value of the heart rate sample data. The systolic pressure SBP(t) is calculated by an equation similar to Equation (2), and $\sigma_{SBP(t)}$, is obtained. Considering that the temperate has different influences on the cardiovascular health parameters and that the corresponding obtained rewards are different. a and b are determined as penalty coefficient which satisfy a>b, specifically as shown by Equations (6) and (7).

$$r_{SBP(t)} = \begin{cases} -a[\overline{SBP(t)} - 90]^2, & \text{if } \overline{SBP(t)} < 90 \text{ mmHg} \\ -a[\overline{SBP(t)} - 140]^2, & \text{if } \overline{SBP(t)} > 140 \text{ mmHg} \\ 0, & \text{if } 90 \text{ mmHg} \le \overline{SBP(t)} \le 140 \text{ mmHg} \end{cases} \quad (6)$$

$$r_{RH(t)} = \begin{cases} -b[\overline{RH(t)} - 55]^2, & \text{if } \overline{RH(t)} < 55 \text{ beats/min} \\ -b[\overline{RH(t)} - 80]^2, & \text{if } \overline{RH(t)} > 80 \text{ beats/min} \\ 0, & \text{if } 55 \text{ beats/min} \le \overline{RH(t)} \le 80 \text{ beats/min} \end{cases} \quad (7)$$

Running control management is performed on the indoor heating, ventilation and air conditioning system in the building based on the state variables, the action variable and the reward function described above.

(3) A collected sample data which will be used to predict is imported to the Q-learning model for running.

A policy for an agent to make decision is selected as F greedy policy. The agent performs a random action with the probability of F and performs the greedy policy with the probability of 1−ε each time, where ε∈(0, 1). For example, when ε=0.1, it is 90% that the agent will select a corresponding action according to the existing optimal value in the Q table, and it is 10% that the agent will select a random action. The use of the ε greedy policy can guarantee that each state space is accessed with a certain probability.

The agent selects a corresponding action in a certain state and updates the value of Q by the following equation:

$$Q(S_t, A_t) \leftarrow Q(S_t, A_t) + \alpha[R_{t+1} + \gamma \max_a Q(S_{t+1}, a) - Q(S_t, A_t)],$$

where $S_{t+1}$ represents next state observed after an action policy is performed in the current state; $R_{t+1}$ represents a reward obtained; and the values of system states s and q are updated.

The Q table (namely, a value function under a corresponding state and action) is updated. It helps the agent to determine what action is selected in each state to obtain the optimal reward.

Cyclic traversal is performed on the first four steps, until s is in a state of termination.

Whether the learning process converges is determined based on the Q table and a learning number threshold. The parameters α and γ can be adjusted in combination with running of the model, which allows the whole learning process to realize better convergence effect.

The above steps are repeated for n times until an optimal policy set π having a maximum cumulative reward value R, namely a control running policy, is obtained by learning.

In this example, using the control policy learned by the Q-learning model, the running policy for the indoor thermal environment control equipment is obtained in combination with the state changes of the cardiovascular physiological health parameters of the aged. It is helpful to create comfortable indoor thermal environment more suitable for the aged. The model-free control method provides effective guidance for improving of the quality of the indoor thermal environment for the aged. It also provides a technical idea for creating healthy and comfortable indoor thermal environment in the aged care building.

On the basis of the above example, the technical features involved therein and the functions and effects of the technical features in the present disclosure are continuously described in detail herein to help those skilled in the art to fully understand and reproduce the technical solutions of the present disclosure.

Finally, although this description is made in accordance with the embodiments, not every embodiment includes only one independent technical solution. Such a description is merely for the sake of clarity. Those skilled in the art should take the description as a whole. The technical solutions in the embodiments can also be appropriately combined to form other embodiments which are comprehensible for those skilled in the art.

What is claimed is:

1. A Q-learning based model-free control method for an indoor thermal environment of an aged care building, comprising the following steps:
   S1: determining related influencing factors for the indoor thermal environment and influencing factors for cardiovascular health of an aged, the related influencing factors for the indoor thermal environment comprising a controlling variable and a controlled variable for a thermal environment in a room and the influencing factors for the cardiovascular health of the aged comprising a systolic pressure and a heart rate, wherein the aged refers to a population aged 65 years old or above; and preprocessing collected data as training sample data;
   S2: constructing a building indoor thermal environment control model and setting an indoor temperature between 18° C. and 24° C.;
   S3: constructing a Q-learning model, specifying a state variable and an action variable of control and a constraint and a reward and punishment mechanism of a state and action value function, and training the Q-learning model with the training sample data to obtain a trained Q-learning model; and
   S4: importing data to be processed to the trained Q-learning model as learning samples and obtaining an optimal control running policy by iterative updating and repeated training.

2. The model-free control method according to claim 1, wherein S1 comprises:
   S1-1: determining cardiovascular health parameters associated with the indoor thermal environment and selecting the systolic pressure and the heart rate as real-time monitoring data; and
   S1-2: analyzing the influencing factors for the indoor thermal environment, determining the controlling variable and the controlled variable of the thermal environment in the room, and collecting indoor temperatures corresponding to time information in the building.

3. The model-free control method according to claim 1, wherein S2 comprises:
   S2-1: considering physiological needs and health characteristics of the aged, assessing the influences of heart rate RH(t) and systolic pressure SBP(t) monitored in real time on the cardiovascular health based on an ideal heart rate range of 55-80 beats per minutes and a normal systolic pressure range of 90-140 mmHg, and deriving a health risk function: Unhealthy=aSBP(t)+bRH(t), wherein a and b are influence coefficients, and a>b;
   calculating a user reward function R by Equation (1):

$$R(t) = \lambda R_{Tin}(t) + \theta R_{Unhealthy}(t) \quad (1)$$

wherein λ and θ are reward factors, $0<\theta<\lambda<1$, representing proportions of the influences of an indoor temperature and cardiovascular health parameters of the aged in optimized control; $\lambda+\theta>1$, ($\lambda>\theta$); $R_{Tin}(t)$ represents a reward value resulting from a change in indoor temperature, and $R_{Unhealthy}(t)$ represents the influences of the cardiovascular health parameters of the aged on state determination of an agent; and S2-2: selecting a standard deviation and a mean value to calculate the values of the heart rate and the systolic pressure within a certain time period, and calculating the standard deviation of the heart rate by Equation (2):

$$\sigma RH(t) = \sqrt{\frac{1}{N-1}\sum_{i=1}^{n}(RH_{(i)} - \overline{RH})^2} \quad (2)$$

wherein N represents the number of heart rate data collected in the time period; i=1, 2, 3, ..., N; $RH_{(i)}$ represents specific heart rate sample data; $\overline{RH}$ represents a mean value of the heart rate sample data.

4. The model-free control method according to claim 1, wherein S3 comprises:

S3-1: importing a collected data set of cardiovascular health parameters of the aged to the Q-learning model for running;

S3-2: selecting, by an agent, ε greedy policy for making decision;

S3-3, updating, by the agent, the value of Q by Equation (3):

$$Q(S_t, A_t) \leftarrow Q(S_t, A_t) + \alpha[R_{t+1} + y_a^{max}Q(S_{t+1}, a) - Q(S_t, A_t)] \quad (3)$$

wherein t is a current time; α is a learning rate, representing a trustworthiness degree of an upgraded portion; γ represents a current attenuation rate of a future value of Q; S represents an environmental state; A represents an action executable by the agent; R represents the reward function; π represents a policy set of the agent;

$S_{t+1}$ represents next state observed after an action policy is performed in a current state; $R_{t+1}$ represents a reward obtained; and S and Q(s,a) are updated;

S3-4: continuously adjusting parameters α and γ in combination with running conditions of the model to optimize a convergence effect of a whole learning process, wherein the whole learning process is determined by a Q table and a learning number threshold; and S3-5: repeating the above steps for n times until an optimal policy set π having a maximum cumulative reward value R.

5. The model-free control method according to claim 1, wherein in S3, the Q-learning model is built by discretizing a continuous state variable and action variable according to a target problem, allowing an agent to continuously interact with the environment to update the Q table using reward values obtained by taking corresponding actions in different states, and obtaining an optimal policy set of accomplishing the target problem by multiple iterations.

6. The model-free control method according to claim 1, wherein in S3, the state and action value function of Q-learning is expressed as:

$$Q(S_t, A_t) \leftarrow Q(S_t, A_t) + \alpha[R_{t+1} + y_a^{max}Q(S_{t+1}, a) - Q(S_t, A_t)] \quad (3)$$

the parameters α and γ are adjusted, wherein $\alpha \in (0,1]$, and $\gamma \in (0,1]$, and therefore, a whole learning process is caused to converge; and the training sample data are input to the Q-learning model for training; the reward values of different actions in different states are updated by iterations until the optimal state and action value function is obtained; and the trained Q-learning model is saved.

* * * * *